(12) United States Patent
Nishioka et al.

(10) Patent No.: US 7,893,254 B2
(45) Date of Patent: Feb. 22, 2011

(54) PROCESS FOR PRODUCTION OF 3-ALKENYLCEPHEM COMPOUNDS

(75) Inventors: Yoichi Nishioka, Tokushima (JP); Masahiro Ito, Tokushima (JP); Yutaka Kameyama, Tokushima (JP)

(73) Assignees: Otsuka Chemical Co., Ltd., Osaka (JP); Meiji Seika Kaisha Ltd., Tokyo (JP)

( * ) Notice: Subject to any disclaimer, the term of this patent is extended or adjusted under 35 U.S.C. 154(b) by 525 days.

(21) Appl. No.: 11/628,248

(22) PCT Filed: Jun. 3, 2005

(86) PCT No.: PCT/JP2005/010621

§ 371 (c)(1), (2), (4) Date: Dec. 1, 2006

(87) PCT Pub. No.: WO2005/118595

PCT Pub. Date: Dec. 15, 2005

(65) Prior Publication Data

US 2008/0033166 A1 Feb. 7, 2008

(30) Foreign Application Priority Data

Jun. 4, 2004 (JP) ............................ 2004-167581

(51) Int. Cl.
*C07D 501/24* (2006.01)
*C07D 501/12* (2006.01)
(52) U.S. Cl. ........................ 540/220; 540/226
(58) Field of Classification Search .................. 540/220
See application file for complete search history.

(56) References Cited

U.S. PATENT DOCUMENTS

| | | | |
|---|---|---|---|
| 3,979,383 A * | 9/1976 | Wild ........................... | 540/220 |
| 4,182,866 A * | 1/1980 | Miki et al. .................. | 540/227 |
| 4,311,698 A * | 1/1982 | Haskell et al. ............. | 514/202 |
| 4,393,058 A * | 7/1983 | Makabe et al. ............. | 514/206 |
| 4,576,938 A * | 3/1986 | Wagatsuma et al. ........ | 514/206 |
| 4,699,979 A | 10/1987 | Hoshi et al. ................. | 540/215 |
| 4,865,823 A * | 9/1989 | Minagawa et al. .......... | 423/112 |
| 5,061,371 A | 10/1991 | Tabata et al. | |
| 5,374,552 A | 12/1994 | Furumai et al. | |
| 5,424,196 A | 6/1995 | Cambiaghi et al. ........... | 435/51 |
| 5,447,719 A * | 9/1995 | Kamataki .................... | 424/741 |
| 5,521,308 A * | 5/1996 | Trodel et al. ................ | 540/226 |
| 5,616,703 A | 4/1997 | Ludescher et al. .......... | 540/226 |
| 5,945,542 A * | 8/1999 | Pollack et al. .............. | 548/497 |
| 6,136,967 A | 10/2000 | Ludescher et al. .......... | 540/215 |
| 6,214,831 B1 * | 4/2001 | Yokoo et al. ................ | 514/257 |
| 6,288,223 B1 | 9/2001 | Okada et al. ................ | 540/220 |
| 6,613,933 B1 | 9/2003 | Nagashima et al. | |
| 6,906,054 B2 | 6/2005 | Buynak et al. | |
| 6,919,457 B2 | 7/2005 | Allerton et al. | |
| 7,087,423 B2 * | 8/2006 | Ehara et al. ................. | 435/242 |
| 7,759,483 B2 * | 7/2010 | Nishioka et al. ............ | 540/220 |
| 2003/0215859 A1 * | 11/2003 | Affholter et al. ............ | 435/6 |
| 2004/0024058 A1 * | 2/2004 | Yamada et al. ............. | 514/513 |
| 2004/0250751 A1 * | 12/2004 | Shimose et al. ............ | 117/84 |
| 2005/0125915 A1 * | 6/2005 | Ichi et al. .................... | 8/438 |
| 2006/0276627 A1 | 12/2006 | Ogura et al. | |
| 2007/0161784 A1 * | 7/2007 | Pollack et al. ............. | 530/414 |
| 2008/0168982 A1 * | 7/2008 | Vente et al. ................. | 127/9 |
| 2008/0249163 A1 * | 10/2008 | Takagaki et al. ............ | 514/456 |
| 2009/0130708 A1 * | 5/2009 | Hashimoto et al. ......... | 435/68.1 |
| 2009/0286284 A1 * | 11/2009 | Murata et al. .............. | 435/88 |
| 2009/0318368 A1 | 12/2009 | Ogura et al. | |

OTHER PUBLICATIONS

"Porosity" <http://en.wikipedia.org/wiki/Porosity> Downloaded from the internet Mar. 3, 2010.*
Food Chemistry, 111(2008) 92-97, Xu, et al.
Kagoshima University, Science Report, No. 33, p. 21-28, 1983 (and Chemical Abstracts abstract).
Abstract from The Journal of Antibiotics, vol. 51, No. 12 (1998), pp. 1081-1086.
Printout from Sorbtech Chromatography (www.sorbtech.com/chromotography/polymericresins/styrenic/tabid/557/default.aspx), 2010.

* cited by examiner

Primary Examiner—Mark L Berch
(74) Attorney, Agent, or Firm—Kubovcik & Kubovcik

(57) ABSTRACT

A process for preparing 7-amino-3-[(E/Z)-2-(4-methylthiazol-5-yl)vinyl]-3-cephem-4-carboxylic acid of the formula (1) and an alkali metal salt thereof, said acid and said salt being improved in the content of 7-amino-3-[(Z)-2-(4-methylthiazol-5-yl)vinyl]-3-cephem-4-carboxylic acid of the formula (2) or an alkali metal salt thereof, the process being characterized in that an aqueous solution of an alkali metal salt of 7-amino-3-[(E/Z)-2-(4-methylthiazol-5-yl)vinyl]-3-cephem-4-carboxylic acid of the formula (1) is treated with a high porous polymer and/or active carbon as added thereto.

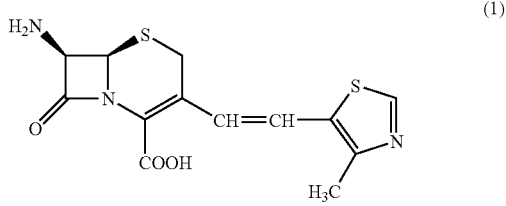

(1)

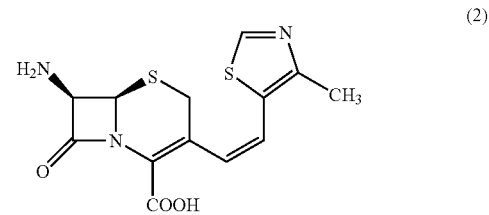

(2)

9 Claims, No Drawings

PROCESS FOR PRODUCTION OF 3-ALKENYLCEPHEM COMPOUNDS

This application is a 371 of international application PCT/JP2005/010621 filed Jun. 3, 2005, which claims priority based on Japanese patent application No. 2004-167581 filed Jun. 4, 2004, which is incorporated herein by reference.

TECHNICAL FIELD

The present invention relates to a process for preparing 7-amino-3-[(Z)-2-(4-methylthiazol-5-yl)vinyl]-3-cephem-4-carboxylic acid and salts thereof.

BACKGROUND ART

An oral cephem agent, cefditoren pivoxil of the formula (5), is in wide used as an antibacterial agent having a broad antimicrobial spectrum and strong antibacterial activities.

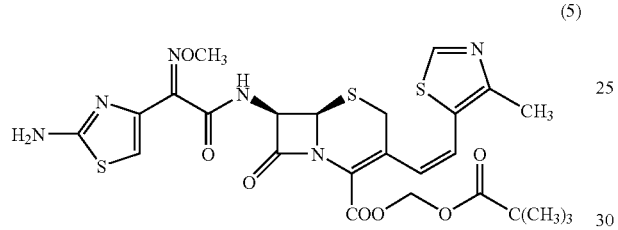

(5)

With cephalosporin antibiotics having alkenyl at the 3-position, the steric structure of the alkenyl group at the 3-position has Z configuration as is the case with cefditoren pivoxil. The mechanism of producing outstanding antibacterial activities on gram-negative bacteria is attributable partly to this feature. For the antibacterial pharmaceutical agent to exhibit its effect, therefore, it is important to diminish to the greatest possible extent the presence of the geometrical E-isomer of cefditoren pivoxil. In preparing cefditoren pivoxil, attempts have been made to improve the Z-isomer content of process intermediates.

For example, a process has been disclosed for preparing an amine salt or hydrochloric acid salt of a Z/E mixture of 7-amino-3-[2-(4-methylthiazol-5-yl)vinyl]-3-cephem-4-carboxylic acid, which is a process intermediate, to deplete the amine salt or hydrochloric acid salt of 7-amino-3-[(E)-2-(4-methylthiazol-5-yl)vinyl]-3-cephem-4-carboxylic acid by adsorption chromatography with an ion exchange resin or active carbon (see, for example, Patent Literature 1)

[Patent Literature 1] JP1995-188250 A

With the process disclosed in the literature, however, Examples 4 and 5 result in E-isomer contents of 14% and 2%, respectively, which are not satisfactory.

In recent years, chromatography is used for separation and purification as industrial means especially in the pharmaceutical industry, but the recovery of the eluent or the regeneration of the adsorbent filling the column heavily burdens the industry, so that the procedure used can not always be an optimum method. Improvements in the purity of pharmaceuticals to be produced and several percent increases in the amount of production are distinctly reflected on the efficacy of the drug and production cost. Thus, high purities and high yields are required of manufacturing processes.

An object of the present invention is to provide an economically outstanding process for preparing 7-amino-3-[(Z)-2-(4-methylthiazol-5-yl)vinyl]-3-cephem-4-carboxylic acid and salts thereof with a minimized E-isomer content.

DISCLOSURE OF THE INVENTION

1. A process for preparing 7-amino-3-[(E/Z)-2-(4-methylthiazol-5-yl)vinyl]-3-cephem-4-carboxylic acid of the formula (1) and an alkali metal salt thereof, said acid and said salt being improved in the content of 7-amino-3-[(Z)-2-(4-methylthiazol-5-yl)vinyl]-3-cephem-4-carboxylic acid of the formula (2) or an alkali metal salt thereof, the process being characterized in that an aqueous solution of an alkali metal salt of 7-amino-3-[(E/Z)-2-(4-methylthiazol-5-yl)vinyl]-3-cephem-4-carboxylic acid of the formula (1) is treated with a high porous polymer and/or active carbon as added thereto.

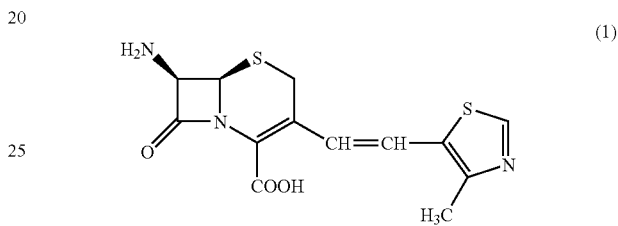

(1)

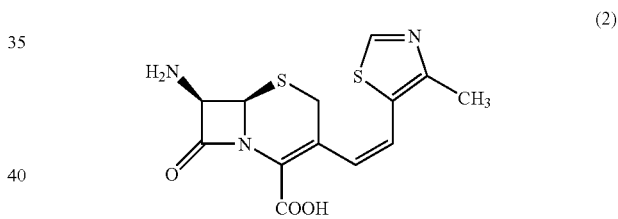

(2)

2. A process for preparing 7-amino-3-[(E/Z)-2-(4-methylthiazol-5-yl)vinyl]-3-cephem-4-carboxylic acid of the formula (1) and an alkali metal salt thereof, said acid and said salt being improved in the content of 7-amino-3-[(Z)-2-(4-methylthiazol-5-yl)vinyl]-3-cephem-4-carboxylic acid of the formula (2) or an alkali metal salt thereof, the process being characterized by subjecting 7-substituted acylamino-3-[(E/Z)-2-(4-methylthiazol-5-yl)vinyl]-3-cephem-4-carboxylic acid compound of the formula (3) to a deprotecting reaction for the carboxylic acid protective group at the 4-position of said compound, treating the resulting compound with an aqueous solution of at least one compound selected from among alkali metal hydroxides, alkali metal hydrogencarbonates and alkali metal carbonates to obtain an alkali metal salt of 7-substituted acylamino-3-[(E/Z)-2-(4-methylthiazol-5-yl)vinyl]-3-cephem-4-carboxylic acid of the formula (4), thereafter subjecting the resulting salt to an enzyme reaction in an aqueous solution and treating an aqueous solution of an alkali metal salt of 7-amino-3-[(E/Z)-2-(4-methylthiazol-5-yl)vinyl]-3-cephem-4-carboxylic acid of the formula (1) obtained with a high porous polymer and/or active carbon as added thereto

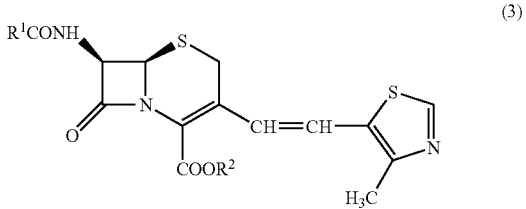

wherein $R^1$ is benzyl or phenoxymethyl, and $R^2$ is carboxylic acid protective group

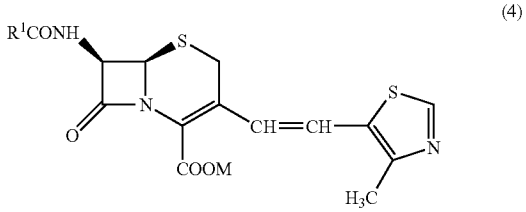

wherein $R^1$ is as defined above, and M is an alkali metal.

We have conducted intensive research and surprisingly found that the Z isomer can be obtained easily in a high yield by treating 7-amino-3-[(E/Z)-2-(4-methylthiazol-5-yl)vinyl]-3-cephem-4-carboxylic acid as converted to an alkali metal salt thereof with a high porous polymer and/or active carbon.

According to the present invention, examples of preferred alkali metal atoms represented by M are a lithium atom, sodium atom and potassium atom, among which sodium atom and potassium atom are especially preferable from the viewpoint of economy.

According to the present invention, the E-isomer can be removed with extremely high selectivity merely by treating, for a short period of time, an aqueous solution of an alkali metal salt of 7-amino-3-[(E/Z)-2-(4-methylthiazol-5-yl)vinyl]-3-cephem-4-carboxylic acid with a high porous polymer and/or active carbon as added directly thereto. It is desirable to stir the aqueous solution with the high porous polymer and/or active carbon added thereto, because the removal of the E-isomer can further be promoted.

The 7-amino-3-[(E/Z)-2-(4-methylthiazol-5-yl)vinyl]-3-cephem-4-carboxylic acid of the formula (1) for use in the present invention is a known compound and is not limited particularly in E-isomer content. However, to obtain the compound of the formula (1) having an improved Z-isomer content, it is desirable that the E-isomer content be about 1 to about 30%, preferably about 1 to about 20%, more preferably about 1 to about 18%. Since further improvements in Z-isomer content can be expected by repeating the present process, the E-isomer content may be less than 1%.

The aqueous solution of an alkali metal salt of the compound of the formula (1) can be readily obtained by treating the corresponding 7-amino-3-[(E/Z)-2-(4-methylthiazol-5-yl)vinyl]-3-cephem-4-carboxylic acid with an aqueous solution of sodium hydroxide, potassium hydroxide, lithium hydroxide or like alkali metal hydroxide, sodium hydrogencarbonate or like alkali metal hydrogencarbonate, or sodium carbonate, potassium carbonate, lithium carbonate or like alkali metal carbonate. Alternatively, the aqueous solution containing a compound of the formula (1') and resulting from the production process of the reaction scheme 1 to be described later can be used as it is.

According to the invention, the concentration of the aqueous solution of alkali metal salt of the compound of the formula (1) is not always important insofar as the alkali metal salt of the compound of the formula (1) can be fully dissolved, and may be determined suitably.

The high porous polymer to be used in this invention is not limited specifically. Examples of such polymers are those wherein the base structure comprises a resin of the methacrylic acid ester copolymer type or like acrylic resin, a resin of the phenol-novolak type or like phenolic resin, or a resin of the styrene-divinylbenzene copolymer type or like styrene resin. Preferable among such resins are high porous polymers wherein the base structure comprises a styrene resin. More preferable are those having a specific surface area of at least 400 $m^2/g$, especially 400 to 1000 $m^2/g$. Examples of such high porous polymers are HP-20 and SP-207, products of Mitsubishi Chemical Corp., XAD-1180 and XAD-1600, products of Rohm-Haas Company, Amberchrom CG-161, product of Tosoh-Haas, etc. These polymers may be used singly, or at least two of them are usable in mixture.

The high porous polymer is used in an amount of 0.1 to 5 parts by weight, preferably 0.3 to 4 parts by weight, more preferably about 0.5 to about 3 parts by weight, per part by weight of the compound of the formula (1). The temperature to be maintained for the treatment is −20 to 50° C., preferably −10 to 30° C., more preferably 0 to 10° C. To achieve a satisfactory result, the treatment is conducted for several minutes to about 2 hours. After the treatment, the high porous polymer can be separated off by a usual method such as filtration or centrifuging.

The active carbon to be used in this invention can be any kind, such as zinc chloride carbon or steam carbon. Any common active carbon is usable without any limitation. Such carbons may be used in mixture.

The active carbon is used in an amount of 0.1 to 5 parts by weight, preferably 0.3 to 4 parts by weight, more preferably about 0.5 to about 3 parts by weight, per part by weight of alkali metal salt of the compound of the formula (1) The water content of the active carbon is not particularly limited either. The active carbon may contain 50% of water, or may be a dry carbon with a water content of about 10%. The temperature to be maintained for the treatment is −20 to 50° C., preferably −10 to 30° C., more preferably 0 to 10° C. To achieve a satisfactory result, the treatment is conducted-for several minutes to about 2 hours. After the treatment, the active carbon can be separated off by a usual method such as filtration or centrifuging.

An acid, such as hydrochloric acid, is added to the aqueous solution of alkali metal salt of the compound of the formula (1) which comprises an improved content of 7-amino-3-[(Z)-2-(4-methylthiazol-5-yl)vinyl]-3-cephem-4-carboxylic acid of the formula (2) to adjust the pH of the solution to 3.0 to 4.3. This affords the compound of the formula (1) which comprises a higher content of the Z-isomer compound of the formula (2). The compound of the formula (1) separates out in water as crystals, which are separated off by a usual method, such as filtration or centrifuging. The separated product is washed with water, and acetone for promoted drying, and further dried, whereby the compound is obtained.

Through one reaction, the process of the invention affords 7-amino-3-[2-(4-methylthiazol-5-yl)vinyl]-3-cephem-4-carboxylic acid having an E-isomer content of less than 0.1% (wt. %, the same as hereinafter) and an extremely high Z-isomer content of at least 99%, preferably 99 to 100%, more preferably 99.5 to 99.99%, 99.75 to 99.96, or 99.9 to 99.95%.

The present invention further gives the Z-isomer in a high yield. The content of the Z-isomer can be improved by repeating the reaction. The term "E-isomer content" as used herein means the proportion of the E-isomer present in the combined amount of the E-isomer and the Z-isomer. The E-isomer content is given by the following equation.

E-isomer content (%)=100×(amount of E-isomer present)/{(amount of E-isomer present)+(amount of Z-isomer present)}

The alkali metal salt [compound of the formula (1')] of 7-amino-3-[(E/Z)-2-(4-methylthiazol-5-yl)vinyl]-3-cephem-4-carboxylic acid of the formula (1) for use in the present invention can be prepared, for example, according to the following reaction scheme 1.

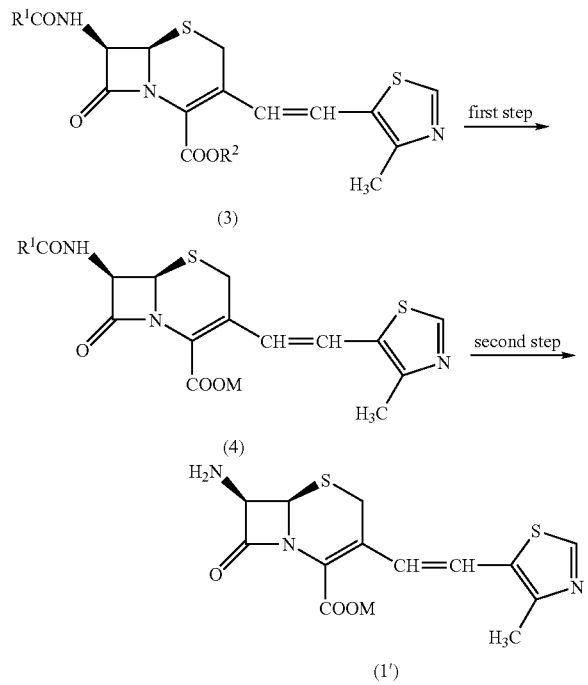

wherein $R^1$ is benzyl or phenoxymethyl, $R^2$ is a carboxylic acid protective group, and M is an alkali metal.

According to the reaction scheme 1, a deprotecting reaction (first step) is conducted for the carboxylic acid protective group at the 4-position of the 7-substituted acylamino-3-[(E/Z)-2-(4-methylthiazol-5-yl)vinyl]-3-cephem-4-carboxylic acid compound of the formula (3) to obtain an alkali metal salt of 7-substituted acylamino-3-[(E/Z)-2-(4-methylthiazol-5-yl)vinyl]-3-cephem-4-carboxylic acid of the formula (4). A reaction is then conducted for removing the substituted acyl group at the 7-position (second step) to produce an alkali metal salt of 7-amino-3-[(E/Z)-2-(4-methylthiazol-5-yl)vinyl]-3-cephem-4-carboxylic acid of the formula (1') for use in the invention.

The carboxylic acid protective group represented by $R^2$ is not limited particularly but can be a known one. Examples of such groups are those given in Theodora W. Greene, "Protective Groups in Organic Synthesis," John Wiley & Sons. Inc., 1981, chap. 5 (pp. 152-192). Preferable among these are a benzyl group which may have an electron-donating group as a substituent on the phenyl ring, and a diphenylmethyl group which may have an electron-donating group on the phenyl ring. Examples of electron-donating groups are methyl, ethyl, tert-butyl and like alkyl groups having 1 to 6 carbon atoms, hydroxyl, and methoxyl, ethoxyl and like alkoxyl groups having 1 to 6 carbon atoms. Diphenylmethyl groups may include those of the type wherein substituted or unsubstituted phenyl groups are linked within the molecule by a methylene ring or hetero atom. Specific examples of benzyl groups which may have an electron-donating group as a substituent on the phenyl ring, and diphenylmethyl groups which may have an electron-donating group as a substituent on the phenyl ring are benzyl, p-methoxybenzyl, o-methoxybenzyl, diphyenylmethyl, 3,4,5-trimethoxybenzyl, 3,5-dimethoxy-4-hydroxybenzyl, 2,4,6-trimethylbenzyl, piperonyl, ditolylmethyl, naphthylmethyl, 9-anthryl, etc. Especially preferable among these from an economical viewpoint are p-methoxylbenzyl and diphenylmethyl which are readily available.

Various methods generally known of the reaction for removing the carboxylic acid protective group of β-lactam compounds can be utilized for the reaction of the first step. For example, already known are a catalytic reduction method using a noble metal catalyst, and a method of treatment with an acid. Also known as methods of the latter type are a method wherein trifluoroacetic acid is used [J. Am. Chem. Soc., 91, 5674 (1969)], a method wherein formic acid is used [Chem. Pharm. Bull. 30, 4545 (1982)], a method of causing aluminum chloride to act on the protective group in the presence of anisole [Tetrahedron Lett. 2793(1979)], etc. Especially superior in view of economy and the ease of the procedure is a method of effecting the deprotecting reaction in a phenol (JP1994-4638B).

Examples of suitable phenols for use in the deprotecting reaction of the first step for the carboxylic acid protective group at the 4-position are phenol, chlorophenol, cresol, methoxyphenol, naphthol, etc. These phenols are used singly, or at least two of them are usable in mixture. The phenol to be used in the present process has the function not only of a reagent but also of a solvent, so that especially preferred are phenol and cresol having a low melting point. In the case where phenols are used, auxiliary solvents are usable which include, for example, water, methylene chloride, chloroform and like hydrocarbon halide solvents, acetone, methyl ethyl ketone, methyl isobutyl ketone and like ketone solvents, ethyl acetate, butyl acetate and like ester solvents, etc. These solvents are used singly or in mixture, as admixed with phenols in an amount of up to 50% based thereon. It is suitable to use phenols in an amount of 0.5 to 500 parts by weight, preferably 1 to 200 parts by weight, more preferably about 1 to about 50 parts by weight, per part by weight of the compound of the formula (3). Although the reaction temperature varies with the kind of phenol to be used and can not be determined specifically, it is advantageous to conduct the reaction at −20 to 100° C., preferably −10 to 70° C., more preferably 0 to 60° C. in view of the stability of the reactant and the product. The reaction time, which is not limited particularly either, is such that the reaction causes the compound of the formula (3) to disappear almost completely. The reaction terminates generally in about 0.5 to about 12 hours. The reaction can be completed within a shortened period of time by adding a catalytic amount of an acid to the reaction system. Examples of suitable acid catalysts are hydrochloric acid, sulfuric acid, perchloric acid, phosphoric acid, formic acid, acetic acid, trifluoroacetic acid, methanesulfonic acid, benzenesulfonic acid, p-toluenesulfonic acid, etc. These catalysts may be used singly, or at least two of them are usable in mixture. Although variable slightly, the amount of catalyst to be used is generally 0.01 to 100 mole %, preferably 0.01 to 50 mole %, more preferably 0.01 to 10 mole %, based on the compound of the formula (3). After the completion of the reaction, the compound of the formula (4) can be obtained easily by the usual extraction procedure. For example, to the solution resulting from the reaction are added an organic solvent such as methyl ethyl ketone, methyl isobutyl ketone or like ketone solvent, ethyl acetate, butyl acetate or like ester solvent, methylene chloride, chloroform or like hydrocarbon halide solvent, benzene, toluene or like aromatic hydrocarbon solvent, or diethyl ether, diisopropyl ether or like ethereal solvent, and also an aqueous layer such as aqueous sodium hydroxide solution, aqueous potassium hydroxide solution, aqueous lithium hydroxide solution or like aqueous alkali metal hydroxide solution, aqueous sodium hydrogencarbonate solution, aqueous sodium carbonate solution, aqueous potassium carbonate solution, aqueous lithium carbonate solution or like aqueous alkali metal salt solution, whereby the alkali metal salt of the formula (4) can be easily obtained in the form of an aqueous solution, with the phenol removed as transferred to the organic solvent layer.

An enzyme reaction is favorably used for the reaction of the second step. The substituted acyl group at the 7-position can be removed by an enzyme reaction easily in a nearly quantitative yield. To render the enzyme active for a prolonged period of time, the reaction is conducted usually in an aqueous system. Since the first step affords the compound of the formula (4) in the form of an aqueous solution of alkali metal salt, the reaction is conducted with penicillin G acylase enzyme (termed also penicillin G amidase enzyme) added directly to the aqueous solution until the compound of the formula (4) disappears almost completely, while with the reaction temperature and the pH maintained in the respective predetermined ranges. Examples of penicillin G amidases enzymes are penicillin G acylases PGA-150, PGA-300 and PGA-450, products of BOEHRINGER MANNHEIM; penicillin G acylase (enzyme), product of DALAS BIOTECH LIMITED; penicillin G amidase, product of Roche Molecular Biochemicals; SynthaCLEC-PA, product of Altus Biologics Inc.; etc. The reaction proceeds nearly quantitatively to give an alkali metal salt of 7-amino-3-[(E/Z)-2-(4-methylthiazol-5-yl)vinyl]-3-cephem-4-carboxylic acid of the formula (1').

The enzyme is used in an amount of 0.1 to 5 parts by weight, preferably 0.3 to 1 part by weight, more preferably about 0.4 to about 0.7 part by weight, per part by weight of the compound of the formula (4). The reaction temperature varies with the kind of enzyme to be used, can not be determined specifically but can be 10 to 50° C., preferably 15 to 40° C., more preferably 20 to 35° C. The pH for the reaction varies with the kind of enzyme to be used, can not be determined specifically but is 7.0 to 9.5, preferably 7.3 to 9.0, more preferably 7.5 to 8.8. The reaction time is not limited particularly but may be such that the compound of the formula (4) is allowed to disappear almost completely. Although dependent on the reaction temperature and pH, the reaction terminates generally in about 0.5 to about 12 hours. As the reaction proceeds, the reaction produces a phenyl acetic acid derivative and therefore reduces the pH of the reaction system. In order to hold the pH of the reaction system within a predetermined range, an aqueous sodium hydroxide solution, aqueous potassium hydroxide solution, aqueous lithium hydroxide solution or like aqueous alkali metal hydroxide solution, or aqueous sodium hydrogencarbonate solution, aqueous sodium carbonate solution, aqueous potassium carbonate solution, aqueous lithium carbonate solution or like aqueous alkali metal carbonate solution, or the like is added to the system. These solutions are used singly, or at least two of them are used in mixture. After the completion of the reaction, the enzyme is separated off by usual separating means as by filtration or centrifuging, affording an alkali metal salt in the form of an aqueous mother liquor separated.

The production process represented by the reaction scheme 1 provides an alkali metal salt of 7-amino-3-[(E/Z)-2-(4-methylthiazol-5-yl)vinyl]-3-cephem-4-carboxylic acid of the formula (1') in the form of an aqueous solution. Accordingly, the compound of the formula (1') need not be isolated by crystallization and separation when the process of the invention is to be applied thereto.

The process for preparing a compound of the formula (1') and further a compound of the formula (1) from a compound of the formula (3) shown in the reaction scheme 1, by way of a compound of the formula (4) is novel and is desirable since the aqueous solution obtained is usable as it is.

BEST MODE OF CARRYING OUT THE INVENTION

The present invention will be described below in detail with reference to Reference Example, Examples and Test Example. However, the invention is in no way limited to Examples.

For a better understanding of the invention, Examples, Comparative Examples and Reference Example are given below.

Incidentally, compounds of the formula (1) will be referred to as compounds (1), compounds of the formula (1') as compounds (1'), compounds of the formula (2) as compounds (2), compounds of the formula (3) as compounds (3), and compounds of the formula (4) as compounds (4).

The E-isomer contents and the Z-isomer content in Examples were each calculated from the foregoing equation using the corresponding area value obtained by HPLC as the amount of the isomer present. The measurement conditions are as follows.

a) Application to the Compound (3)

Column [YMC-AM312 (ODS) 6.0 diam×150 mm], column temp. (constant temp. around 25° C.), mobile phase (acetonitrile/buffer=50/50, buffer: prepared by dissolving 7.29 g of $NaH_2PO_4.2H_2O$ and 0.464 g of $Na_2HPO_4$ in 1 liter of distilled water), flow rate (1.0 ml/min.), detecting wavelength (274 nm), injection (10 μl), scanning time: 45 min., Z-isomer retention time (16-17 min.), E-isomer retention time (21-22 min.).

b) Application to the Compounds (1) and (2)

Column [Waters Symmetry Shield RP 8 5 μm (4.6 diam× 250 mm)], column temp. (constant temp. around 30° C.), mobile phase (acetonitrile/buffer=3/97, buffer: prepared by dissolving 2.9 g of $NH_4H_2PO_4$ in about 900 ml of distilled water, adjusting the solution to a pH of 2.0 with phosphoric acid and adjusting the volume of the solution accurately to 1 liter by addition of distilled water), flow rate (1.0 ml/min.), detecting wavelength (254 nm), injection (10 μl), scanning time: 30 min., Z-isomer retention time (6.5-7.5 min.), E-isomer retention time (9.5-10.5 min.).

EXAMPLE 1

[Procedure 1]

A 10 g quantity of a compound (3) ($R^1$=benzyl, $R^2$=diphenylmethyl) having an E-isomer content of 10% was measured out and placed into a 500-ml four-necked flask, and 55 ml of phenol was further placed in, followed by stirring at 50 to 55° C. for 5 hours. To the reaction mixture were added 100 ml of ethyl acetate and 200 ml of 5% aqueous sodium hydrogencarbonate solution, and the mixture was thereafter cooled to not higher than 10° C. The organic layer was removed, and the aqueous layer was collected and washed with 150 ml of ethyl acetate three times, giving an aqueous solution of a compound (4) ($R^1$=benzyl, M=sodium). To the solution was added 5 g of PGA-450, followed by a reaction at 20 to 30° C. for 3 hours while the mixture was being adjusted to a pH of 7.5 to 8.5 with a 5% aqueous sodium carbonate solution. After the completion of the reaction, the enzyme was filtered off, and an aqueous solution of a compound (1') (M=sodium) was obtained in a flask. Present in the aqueous solution was the compound (1') having an E-isomer content of 10% in an amount corresponding to 4.77 g (84.0% in yield).

[Procedure 2]

The aqueous solution was cooled to not higher than 10° C. and thereafter stirred for 1 hour with the addition of 5 g of active carbon. The active carbon was filtered off, and the filtrate was adjusted to a pH of 4.0 with 4N hydrochloric acid and aged at a temperature of up to 10° C. for 1 hour. The crystals separating out were collected by filtration, washed with water and acetone and dried, affording a compound (1) with an improved content of compound (2).

Yield: 3.82 g

Yield of Z-isomer: 95.0% (procedure 2), 79.8% (procedures 1 and 2)

E-isomer content: 0.09% (Z-isomer content: 99.91%)

$^1$H-NMR(0.2 mol/L-DCl/$D_2O$ ppm from TSP): 2.53(3H, s, $CH_3$), 3.56-3.61(1H, d, S—CH(H), 18.4 Hz), 3.75-3.80(1H, d, S—CH(H), 18.4 Hz), 5.26-5.27(1H, d, S—CH, 5.2 Hz), 5.45-5.46(1H, d, N—CH, 5.2 Hz), 6.79(2H, s, HC=CH), 9.79(1H, s, S—CH=N)

EXAMPLE 2

[Procedure 1]

A 10 g quantity of a compound (3) ($R^1$=benzyl, $R^2$=p-methoxybenzyl) having an E-isomer content of 9% was measured out and placed into a 500-ml four-necked flask, and 60 ml of cresol was further placed in, followed by stirring at 45 to 50° C. for 10 hours. To the reaction mixture were added 100 ml of butyl acetate and 200 ml of 5% aqueous sodium hydrogencarbonate solution, and the mixture was thereafter cooled to not higher than 10° C. The organic layer was removed, and the aqueous layer was collected and washed with 150 ml of butyl acetate three times, giving an aqueous solution of a compound (4) ($R^1$=benzyl, M=sodium). To the solution was added 5 g of PGA-450, followed by a reaction at 20 to 30° C. for 3 hours while the mixture was being adjusted to a pH of 7.5 to 8.5 with a 5% aqueous sodium carbonate solution. After the completion of the reaction, the enzyme was filtered off, and an aqueous solution of a compound (1') (M=sodium) was obtained in a flask. Present in the aqueous solution was the compound (1') having an E-isomer content of 9% in an amount corresponding to 5.29 g (86.0% in yield).

[Procedure 2]

The aqueous solution was cooled to not higher than 10° C. and thereafter stirred for 1 hour with the addition of 4.5 g of active carbon. The active carbon was filtered off, and the filtrate was adjusted to a pH of 4.0 with 4N hydrochloric acid and aged at a temperature of up to 10° C. for 1 hour. The crystals separating out were collected by filtration, washed with water and acetone and dried, affording a compound (1) with an improved content of compound (2). The structure of the compound (1) was confirmed by $^1$H-NMR.

Yield: 4.30 g

Yield of Z-isomer: 95.5% (procedure 2), 82.1% (procedures 1 and 2)

E-isomer content: 0.08% (Z-isomer content: 99.92%)

EXAMPLE 3

[Procedure 1]

A 10 g quantity of a compound (3) ($R^1$=phenoxymethyl, $R^2$=p-methoxybenzyl) having an E-isomer content of 15% was measured out and placed into a 500-ml four-necked flask, and 50 ml of a solvent mixture, phenol/cresol (1/1), was further placed in, followed by stirring at 50 to 60° C. for 4 hours. To the reaction mixture were added 100 ml of methyl isobutyl ketone and 200 ml of 5% aqueous sodium hydrogencarbonate solution, and the mixture was thereafter cooled to not higher than 10° C. The organic layer was removed, and the aqueous layer was collected and washed with 150 ml of methyl isobutyl ketone three times, giving an aqueous solution of a compound (4) ($R^1$=phenoxymethyl, M=sodium). To the solution was added 5 g of PGA-450, followed by a reaction at 25 to 30° C. for 4 hours while the mixture was being adjusted to a pH of 7.7 to 8.7 with a 5% aqueous sodium carbonate solution. After the completion of the reaction, the enzyme was filtered off, and an aqueous solution of a compound (1') (M=sodium) was obtained. Present in the aqueous solution was the compound (1') having an E-isomer content of 15% in an amount corresponding to 4.84 g (80.9% in yield).

[Procedure 2]

The aqueous solution was cooled to not higher than 10° C. and thereafter stirred for 1 hour with the addition of 6 g of active carbon. The active carbon was filtered off, and the filtrate was adjusted to a pH of 4.0 with 4N hydrochloric acid and aged at a temperature of up to 10° C. for 1 hour. The crystals separating out were collected by filtration, washed with water and acetone and dried, affording a compound (1) with an improved content of compound (2). The structure of the compound (1) was confirmed by $^1$H-NMR.

Yield: 3.56 g

Yield of Z-isomer: 92.5% (procedure 2), 74.8% (procedures 1 and 2)

E-isomer content: 0.10% (Z-isomer content: 99.90%)

EXAMPLE 4

[Procedure 1]

A 10 g quantity of a compound (3) ($R^1$=phenoxymethyl, $R^2$=diphenylmethyl) having an E-isomer content of 12% was measured out and placed into a 500-ml four-necked flask, and 45 ml of phenol was further placed in, followed by stirring at 55 to 60° C. for 4 hours. To the reaction mixture were added 100 ml of methyl ethyl ketone and 200 ml of 3% aqueous potassium carbonate solution, and the mixture was thereafter cooled to not higher than 10° C. The organic layer was removed, and the aqueous layer was collected and washed with 150 ml of methyl ethyl ketone three times, giving an aqueous solution of a compound (4) ($R^1$=phenoxymethyl, M=sodium). To the solution was added 5 g of PGA-450, followed by a reaction at 25 to 30° C. for 4 hours while the mixture was being adjusted to a pH of 7.7 to 8.7 with a 5% aqueous potassium carbonate solution. After the completion of the reaction, the enzyme was filtered off, and an aqueous solution of a compound (1') (M=potassium) was obtained.

Present in the aqueous solution was the compound (1') having an E-isomer content of 12% in an amount corresponding to 4.93 g (85.1% in yield).

[Procedure 2]

The aqueous solution was cooled to not higher than 10° C. and thereafter stirred for 1 hour with the addition of 6 g of active carbon. The active carbon was filtered off, and the filtrate was adjusted to a pH of 4.0 with 4N hydrochloric acid and aged at a temperature of up to 10° C. for 1 hour. The crystals separating out were collected by filtration, washed with water and acetone and dried, affording a compound (1) with an improved content of compound (2). The structure of the compound (1) was confirmed by $^1$H-NMR.

Yield: 3.65 g

Yield of Z-isomer: 94.1% (procedure 2), 80.0% (procedures 1 and 2)

E-isomer content: 0.10% (Z-isomer content: 99.90%)

EXAMPLE 5

[Procedure 1]

A 10 g quantity of a compound (3) ($R^1$=benzyl, $R^2$=2,4,6-trimethylbenzyl) having an E-isomer content of 10% was measured out and placed into a 500-ml four-necked flask, and 50 ml of phenol and 0.1 ml of concentrated hydrochloric acid were further placed in, followed by stirring at 45 to 50° C. for 4 hours. To the reaction mixture were added 200 ml of methylene chloride and 200 ml of 5% aqueous sodium hydrogencarbonate solution, and the mixture was thereafter cooled to not higher than 10° C. The organic layer was removed, and the aqueous layer was collected and washed with 150 ml of methylene chloride five times, giving an aqueous solution of a compound (4) ($R^1$=benzyl, M=sodium). To the solution was added 5 g of PGA-450, followed by a reaction at 20 to 30° C. for 3 hours while the mixture was being adjusted to a pH of 7.5 to 8.5 with a 5% aqueous sodium carbonate solution. After the completion of the reaction, the enzyme was filtered off, and an aqueous solution of a compound (1') (M=sodium) was obtained. Present in the aqueous solution was the compound (1') having an E-isomer content of 10% in an amount corresponding to 5.00 g (83.0% in yield).

[Procedure 2]

The aqueous solution was cooled to not higher than 10° C. and thereafter stirred for 1 hour with the addition of 5 g of active carbon. The active carbon was filtered off, and the filtrate was adjusted to a pH of 4.0 with 4N hydrochloric acid and aged at a temperature of up to 10° C. for 1 hour. The crystals separating out were collected by filtration, washed with water and acetone and dried, affording a compound (1) with an improved content of compound (2). The structure of the compound (1) was confirmed by $^1$H-NMR.

Yield: 4.00 g

Yield of Z-isomer: 95.0% (procedure 2), 78.9% (procedures 1 and 2)

E-isomer content: 0.09% (Z-isomer content: 99.91%)

EXAMPLE 6

A 10 g quantity of a compound (3) ($R^1$=benzyl, $R^2$=diphenylmethyl) having an E-isomer content of 10% was measured out and placed into a 500-ml four-necked flask, and 50 ml of phenol and 0.1 ml of concentrated sulfuric acid were further placed in, followed by stirring at 50 to 55° C. for 3 hours. To the reaction mixture were added 100 ml of ethyl acetate and 300 ml of 5% aqueous sodium hydrogencarbonate solution, and the mixture was thereafter cooled to not higher than 10° C. The organic layer was removed, and the aqueous layer was collected and washed with 150 ml of ethyl acetate three times, giving an aqueous solution of a compound (4) ($R^1$=benzyl, M=sodium). To the solution was added 5 g of PGA-450, followed by a reaction at 20 to 30° C. for 4 hours while the mixture was being adjusted to a pH of 7.5 to 8.3 with a 5% aqueous sodium carbonate solution. After the completion of the reaction, the enzyme was filtered off, and an aqueous solution of a compound (1') (M=sodium) was obtained. Present in the aqueous solution was the compound (1') having an E-isomer content of 10% in an amount corresponding to 4.89 g (86.1% in yield).

[Procedure 2]

The aqueous solution was cooled to not higher than 10° C. and thereafter stirred for 1 hour with the addition of 15 g of a high porous polymer (HP-20). The polymer was filtered off, and the filtrate was adjusted to a pH of 4.0 with 4N hydrochloric acid and aged at a temperature of up to 10° C. for 1 hour. The crystals separating out were collected by filtration, washed with water and acetone and dried, affording a compound (1) with an improved content of compound (2). The compound (1) was confirmed by $^1$H-NMR.

Yield: 3.91 g

Yield of Z-isomer: 94.9% (procedure 2), 81.6% (procedures 1 and 2)

E-isomer content: 0.09% (Z-isomer content: 99.91%)

EXAMPLE 7

[Procedure 1]

A 10 g quantity of a compound (3) ($R^1$=benzyl, $R^2$=p-methoxybenzyl) having an E-isomer content of 9% was measured out and placed into a 500-ml four-necked flask, 30 ml of anisole was placed in, and 100 ml of trifluoroacetic acid was further placed in with ice cooling, followed by stirring at the same temperature for 1 hour. The reaction mixture was concentrated in a vacuum, and to the concentrate were thereafter added 100 ml of butyl acetate and 200 ml of 5% aqueous sodium hydrogencarbonate solution. The mixture was cooled to not higher than 10° C. The organic layer was removed, and the aqueous layer was collected and washed with 150 ml of butyl acetate three times, giving an aqueous solution of a compound (4) ($R^1$=benzyl, M=sodium). To the solution was added 5 g of PGA-450, followed by a reaction at 20 to 30° C. for 3 hours while the mixture was being adjusted to a pH of 7.5 to 8.5 with a 5% aqueous sodium carbonate solution. After the completion of the reaction, the enzyme was filtered off, and an aqueous solution of a compound (1') (M=sodium) was obtained. Present in the aqueous solution was the compound (1') having an E-isomer content of 9% in an amount corresponding to 5.22 g (84.9% in yield).

[Procedure 2]

The aqueous solution was cooled to not higher than 10° C. and thereafter stirred for 1 hour with the addition of 5 g of active carbon. The active carbon was filtered off, and the filtrate was adjusted to a pH of 4.0 with 4N hydrochloric acid and aged at a temperature of up to 10° C. for 1 hour. The crystals separating out were collected by filtration, washed with water and acetone and dried, affording a compound (1) with an improved content of compound (2). The compound (1) was confirmed by $^1$H-NMR.

Yield: 4.25 g

Yield of Z-isomer: 95.5% (procedure 2), 81.1% (procedures 1 and 2)

E-isomer content: 0.09% (Z-isomer content: 99.91%)

REFERENCE EXAMPLE 1

The compounds (1) prepared in Examples 1 to 7 and diminished in E-isomer content can each be converted to cefditoren pivoxil efficiently. Cefditoren pivoxil can be prepared, for example, from the compound (1) obtained in Example 1 by the methods disclosed in Japanese Patent No. 2846186 or Journal of Synthetic Organic Chemistry, Japan, Vol. 60, No. 2, 155-161 (2002).

INDUSTRIAL APPLICABILITY

The production process of the invention converts 7-amino-3-[2-(4-methylthiazol-5-yl)vinyl]-3-cephem-4-carboxylic acig wherein both geometrical E-isomer and Z-isomer are present in mixture is converted to an alkali metal salt, whereby 7-amino-3-[2-(4-methylthiazol-5-yl)vinyl]-3-cephem-4-carboxylic acid and the alkali metal salt thereof can be obtained easily with a high Z-isomer content in high yields.

The invention claimed is:

1. A process for preparing 7-amino-3-[(E/Z)-2-(4-methylthiazol-5-yl)vinyl]-3-cephem-4-carboxylic acid of the formula (1) or an alkali metal salt thereof, said acid or said salt being higher in the weight % content of 7-amino-3-[(Z)-2-(4-methylthiazol-5-yl)vinyl]-3-cephem-4-carboxylic acid of the formula (2) or of an alkali metal salt thereof than the weight % content of a starting salt, the process comprising: providing an aqueous solution of an alkali metal salt of 7-amino-3-[(E/Z)-2-(4-methylthiazol-5-yl) vinyl]-3-cephem-4-carboxylic acid of the formula (1), treating said aqueous solution with active carbon as added thereto, and, optionally, adding an acid to said treated aqueous solution to convert the salt into an acid

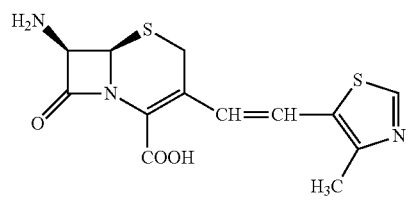

(1)

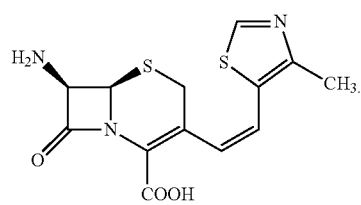

(2)

2. A preparation process according to claim 1 wherein the treatment with the active carbon is conducted with stirring.

3. A process for preparing 7-amino-3-[(E/Z)-2-(4-methylthiazol-5-yl)vinyl]-3-cephem-4-carboxylic acid of the formula (1) and an alkali metal salt thereof, said acid or said salt being higher in the weight % content of 7-amino-3-[(Z)-2-(4-methylthiazol-5-yl) vinyl]-3-cephem-4-carboxylic acid of the formula (2) or of an alkali metal salt thereof than the weight % content of a starting salt, the process comprising: subjecting 7-substituted acylamino-3-[(E/Z)-2-(4-methylthiazol-5-yl)vinyl]-3-cephem-4-carboxylic acid compound of the formula (3) to a deprotecting reaction for the carboxylic acid protective group at the 4-position of said compound, treating the resulting compound with an aqueous solution of at least one compound selected from among alkali metal hydroxides, alkali metal hydrogencarbonates and alkali metal carbonates to obtain an alkali metal salt of 7-substituted acylamino-3-[(E/Z)-2-(4-methylthiazol-5-yl)vinyl]-3-cephem-4-carboxylic acid of the formula (4), thereafter subjecting the resulting salt to an enzyme reaction in an aqueous solution to obtain an aqueous solution of an alkali metal salt of 7-amino-3-[(E/Z)-2-(4-methylthiazol-5-yl)vinyl]-3-cephem-4-carboxylic acid of the formula (1) and treating said aqueous solution with active carbon as added thereto, and, optionally, adding an acid to said treated aqueous solution to convert the salt into an acid

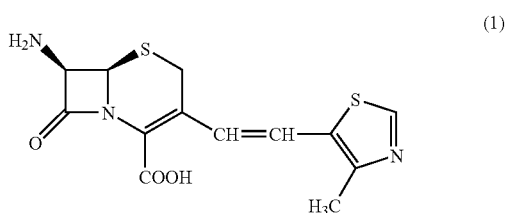

(1)

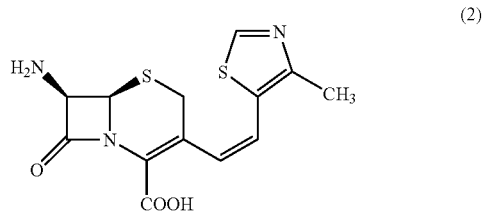

(2)

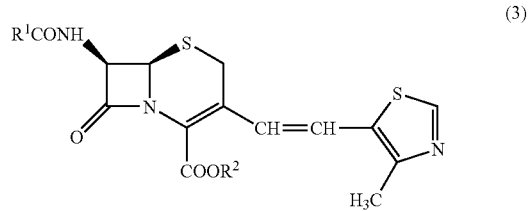

(3)

wherein $R^1$ is benzyl or phenoxymethyl, and $R^2$ is carboxylic acid protective group

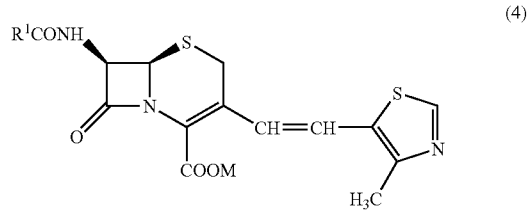

(4)

wherein $R^1$ is as defined above, and M is an alkali metal.

4. A preparation process according to claim 3 wherein the treatment with the active carbon is conducted with stirring.

5. A preparation process according to claim 1 wherein the product resulting from the treatment is at least 99% in the contents of 7-amino-3-[(Z)-2-(4-methylthiazol-5-yl)vinyl]-3-cephem-4-carboxylic acid of the formula (2) and an alkali metal salt thereof.

6. A preparation process according to claim 5 wherein the product resulting from the treatment is at least 99.5% in the contents of 7-amino-3-[(Z)-2-(4-methylthiazol-5-yl)vinyl]-3-cephem-4-carboxylic acid of the formula (2)and an alkali metal salt thereof.

7. A preparation process according to claim 3 wherein the enzyme reaction is conducted with use of a penicillin G acylase at a reaction temperature of 10 to 50° C. and pH of 7.0 to 9.5.

8. A preparation process according to claim 3 wherein the product resulting from the treatment is at least 99% in the contents of 7-amino-3-[(Z)-2-(4-methylthiazol-5-yl)vinyl]-3-cephem-4-carboxylic acid of the formula (2) and an alkali metal salt thereof.

9. A preparation process according to claim 8 wherein the product resulting from the treatment is at least 99.5% in the contents of 7-amino-3-[(Z)-2-(4-methylthiazol-5-yl )vinyl]-3-cephem-4-carboxylic acid of the formula (2) and an alkali metal salt thereof.

* * * * *